United States Patent [19]

Peludat

[11] Patent Number: 5,624,311

[45] Date of Patent: Apr. 29, 1997

[54] METHOD AND APPARATUS FOR ROOM TEMPERATURE EQUALIZING AND AIR TREATMENT

[76] Inventor: Walter W. Peludat, 2218 E. Wattles Rd., Troy, Mich. 48098

[21] Appl. No.: 624,341

[22] Filed: Apr. 3, 1996

Related U.S. Application Data

[63] Continuation of Ser. No. 294,817, Aug. 26, 1994, abandoned.

[51] Int. Cl.$^6$ ............................................. F24F 3/16
[52] U.S. Cl. ............................. 454/230; 422/124
[58] Field of Search .................. 422/124; 454/230, 454/231, 233; 55/467, 471

[56] References Cited

U.S. PATENT DOCUMENTS

| | | | |
|---|---|---|---|
| 2,614,820 | 10/1952 | Boydjieff | 422/124 X |
| 3,850,598 | 11/1974 | Boehm | 454/230 X |
| 4,730,551 | 3/1988 | Peludat . | |
| 5,147,582 | 9/1992 | Hulzner, Sr. et al. | 422/124 X |
| 5,180,332 | 1/1993 | Mitchell et al. | 454/230 |
| 5,223,182 | 6/1993 | Steiner et al. | 422/124 X |
| 5,358,443 | 10/1994 | Mitchell et al. | 454/230 |

FOREIGN PATENT DOCUMENTS 158924  9/1984  Japan ................................ 454/230

*Primary Examiner*—Harold Joyce
*Attorney, Agent, or Firm*—Gifford, Krass, Groh, Sprinkle, Patmore, Anderson & Citkowski, P.C.

[57] ABSTRACT

A method and apparatus for use in a room for circulating the air, for substantially balancing the temperature of the air distributed in the room, and for treating the air. The apparatus comprises a body having an interior cavity. The cavity is provided with an air-circulating fan assembly and air treating component. The air treating component may be hollow and may include filtering, deodorizing, and scenting material. Strategic placement of the apparatus within a room allows for substantially balanced room temperatures.

4 Claims, 3 Drawing Sheets

METHOD AND APPARATUS FOR ROOM TEMPERATURE EQUALIZING AND AIR TREATMENT

This is a continuation of application Ser. No. 08/294,817 filed on Aug. 26, 1994, now abandoned.

BACKGROUND OF THE INVENTION

I. Field of the Invention

The present invention relates to air temperature and air quality control in buildings. More particularly, the present invention relates to a method and apparatus for circulating air in a room, for substantially equalizing the air temperature of a room, and for treating the air of a room.

II. Description on the Relevant Art

Modern office buildings and even many new homes are designed to be more or less sealed boxes, not allowing outside air to enter or exit but through the occasionally opened door. The modern "hermetically-sealed" construction is thought to minimize heating and cooling costs by prohibiting the random opening and closing of windows by office workers. The modern construction also reduces building costs because sealed windows are less costly to make and install than are windows that can be selectively opened and closed.

While proving to save money, the modern design also produces undesirable results, in that the interior air never changes to any significant degree. Workers often complain of what has become known as "sick building syndrome", allegedly caused by dirty office air.

A problem also related to the static nature of air in modern buildings (as well as in older buildings with windows that are openable) is that warm air tends to linger below the ceiling while cooler air remains in the lower half of the room. The floor-to-ceiling temperature difference can vary by a considerable amount and a variance of between 15 and 30 degrees is common. The result is that the warm air is not generally in the area occupied by people, thus requiring the need for higher amounts of heat energy to be used to warm the lower half of the room.

Known approaches to overcoming these problems have failed.

SUMMARY OF THE PRESENT INVENTION

The present invention overcomes the difficulties in economically and practically equalizing air temperature and modifying air quality by providing a method and apparatus for use in a room for circulating the air, for substantially balancing the temperature of the air distributed in the room, and for treating the air.

The apparatus comprises a body having an interior cavity. The body includes an air inlet end and an air outlet end. Circulating air enters one end and is exhausted out the other end. An air-circulating fan fitted within the cavity moves the air.

An air treating component is provided between the inlet end of the body and the outlet end. Moving air passes through the air treating component. The component may comprise a hollow body having a front side and a back side. A plurality of air passageways are defined in the front side and the back side.

Within the hollow body of the component is provided an air treating component. The material may be specifically intended for dust-removal, odor-removal, or scent-provision, or may be any combination of these three. Examples of the material include charcoal and pulverized fruit seed or electrostatic filter to intercept 100% of mold spores and up to 94% of other irritants in indoor air.

To maximize the potential of the apparatus, the selected room must be surveyed so as to identify the best (and most practical) location for its placement. This placement may be on the wall, the ceiling, or the floor. The goal in making the selection is to position the apparatus of the present invention so that air temperature difference between the floor and ceiling are minimized, thus saving on heating and cooling costs. When properly situated, the temperature difference from ceiling to floor at any time during the heating fan on/heating fan off cycle should be no greater than eight degrees, and as little as 2° or 3°.

Other objects and details of the present invention will become apparent from the following detailed description.

BRIEF DESCRIPTION OF THE DRAWINGS

The present invention will be more fully understood by reference to the following detailed description of the preferred embodiments of the present invention, when read in conjunction with the accompanying drawings, in which like reference characters refer to like parts throughout the views, and in which.

DETAILED DESCRIPTION OF THE PREFERRED EMBODIMENTS OF THE PRESENT INVENTION

Figure 1:
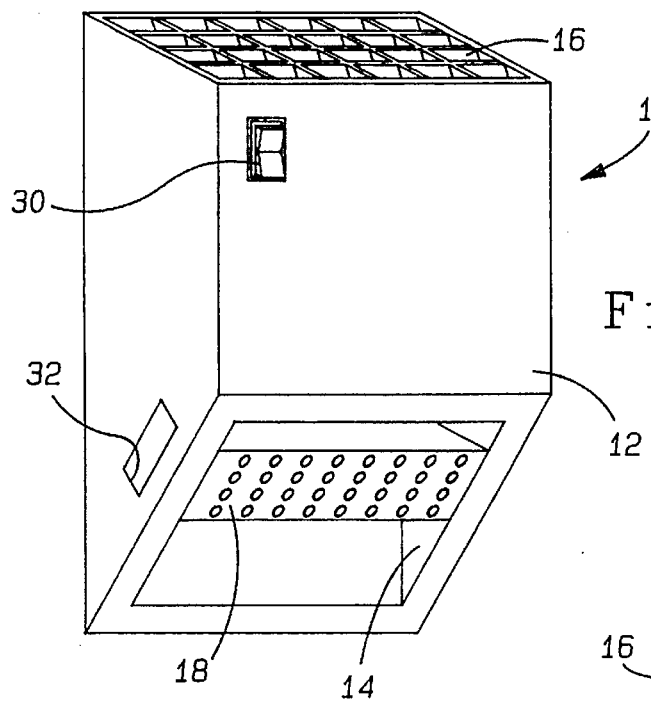
FIG. 1 is a perspective view of the preferred embodiment of the present invention.

The drawing discloses the preferred embodiment of the present invention. While the configurations according to the illustrated embodiments are preferred, it is envisioned that alternate configurations of the present invention may be adapted without deviating from the invention as portrayed. The preferred embodiments are discussed hereafter.

Referring to FIG. 1, an air treater-circulator is shown and generally referred to as 10. The treater-circulator includes a body 12. The body 12 may be composed of a variety of materials, including wood or a plastic. The shape of the body 12, as illustrated, is only a suggested shape, and the invention should not be limited thereby. What is important is that the body 12 have an inlet 14 and an outlet 16. The treater-circulator 10 illustrated in FIG. 1 is preferred for suspension on a wall. Floor and ceiling units according to the present invention are also possible, and these are illustrated below in FIGS. 4 through 7 and are discussed in association therewith.

Disposed within the inlet 14 is an air treating component 18. The component 18 may be either a filter for filtering air or may a deodorizer for deodorizing room air. It may also work as a scenting unit for applying a masking scent as may be desired. In addition, component 18 may accomplish all of these tasks. This would depend on the construction of the component 18, as discussed below with respect to FIG. 3.

Figure 2:
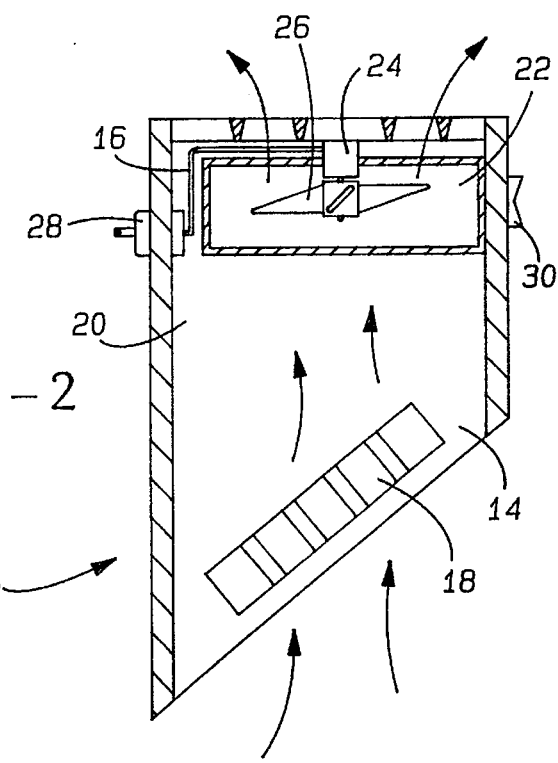
FIG. 2 is a sectional side view of the embodiment of FIG. 1.

With respect to FIG. 2, a sectional view of the treater-circulator 10 is illustrated. The body 12 has a plenum 20 defined within its walls. Within the plenum 20 is provided a fan assembly 22. The fan assembly 22 includes a fan motor 24 and a fan blade 26. A rotatable plug assembly 28 is filled to enable the unit to be plugged directly into a wall plug (not shown). The plug may be rotated to accommodate either vertically- or horizontally-mounted plugs. A switch 30 is filled to close the circuit for fan operation.

The air treating component 18 is illustrated as being disposed substantially across the inlet 14. The component 18 may be easily removed or replaced by sliding through an opening 32 (see FIG. 1) defined in both sides of the body 12.

As illustrated in FIG. 2, the block is disposed on the draw side of the fan assembly 22. In this position the circulated air first passes through the air treating component 18. Alternatively, the air treating component 18 may be disposed on the exhaust side of the fan assembly 22. In either embodiment, it is important that the air circulate one way or the other 30 through the air treating component 18.

Figure 3:
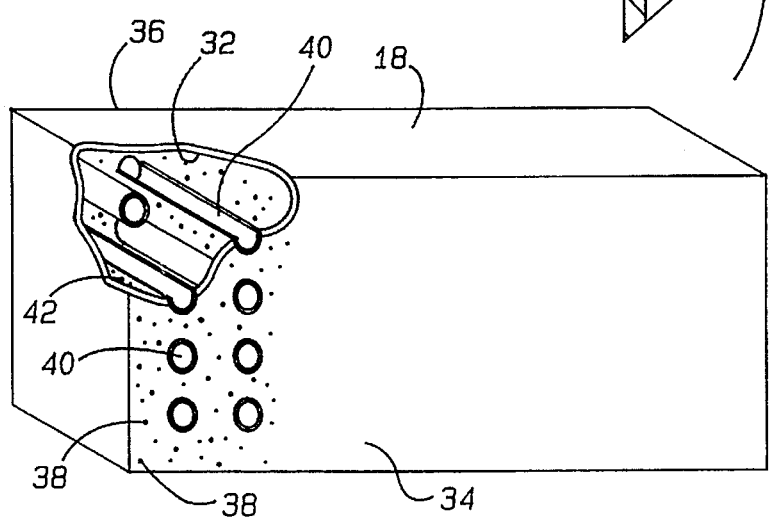
FIG. 3 is a perspective, partially sectioned, view of the preferred air treating component of the present invention.

FIG. 3 is a perspective, partially sectioned, view of the preferred air treating component 18 of the present invention. Although the component 18 is illustrated as being of a substantially rectangular configuration, it may, as well, be provided in other shapes.

The preferred construction of the component 18 is hollow, as illustrated, having an interior space 32 defined by the external walls. A front wall 34 and a back wall 36 (not visible) each has defined therein a plurality of air-passing holes 38. The holes 38 allow for passage of circulated air through the component 18. However, as the treater-circulator 10 is designed for both air treatment as well as circulation, the holes 38 are inadequate to allow for substantial air circulation. (The holes 38 are small to contain the media disposed within the component 18, as discussed below.) Accordingly, a series of passages 40 are provided to allow more air to pass through the component 18.

A media 42 is loosely disposed within the component 18 to accomplish the air treating step of the present invention. The media 42 is preferably granular and loose, thereby providing maximum surface area for air treatment. The media 42 may be charcoal or may be other material, such as baking soda, or even ground fruit seed (preferably grapefruit seed). In any event, it is important that the media 42 be selected to accomplish a specific purpose, whether that purpose be air filtering, deodorizing, or scenting.

In lieu of a hollow block, the air treating component may be composed of a matrix having air treating material (not shown.) For example, a sponge material or a fibrous material may be coated with baking soda.

Figure 4:
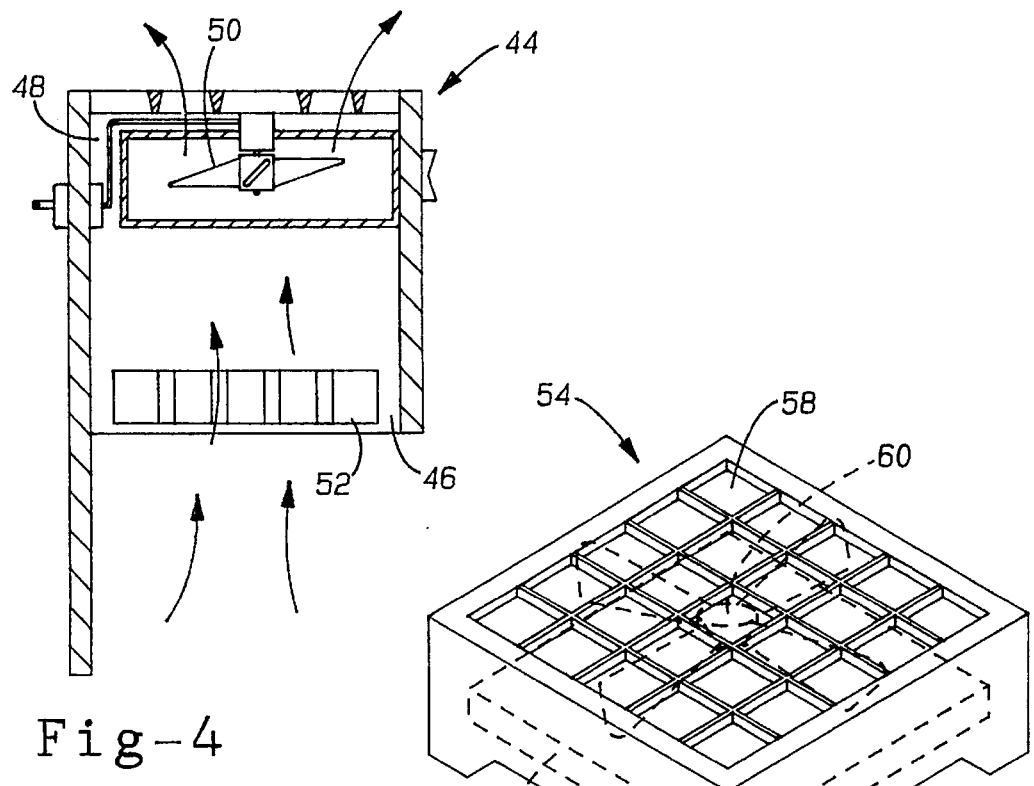
FIG. 4 shows a sectional side view of an alternate embodiment of the wall-mounted apparatus shown in FIG. 1.

Referring to FIG. 4, a variation of the treater-circulator of FIGS. 1 and 2 is illustrated. In this Figure, a treater-circulator, generally indicated as 44, is shown and includes an inlet 46, an outlet 48, a fan assembly 50, and an air treating component 52. Like the treater-circulator 10 of FIG. 1, the illustrated model of FIG. 4 is also a wall unit.

Figure 5:
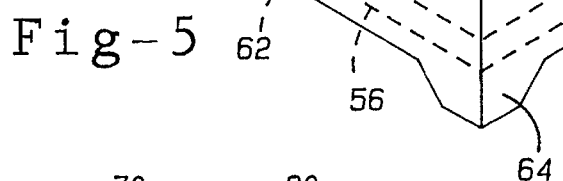
FIG. 5 is a perspective view of another alternate embodiment of the present invention, this style being used for placement on a floor.

FIG. 5 illustrates an alternate embodiment of the present invention for disposition on the floor of a room. According to this embodiment, a treater-circulator, generally illustrated as 54, is shown. The treater-circulator 54 has an inlet 56, an outlet 58, a fan assembly 60, and an air treating component 62. A plurality of legs 64 are provided to allow clearance for the inlet 56. The construction and function of the component 62 is substantially the same as that shown and discussed above with respect to FIG. 3.

Figure 6:
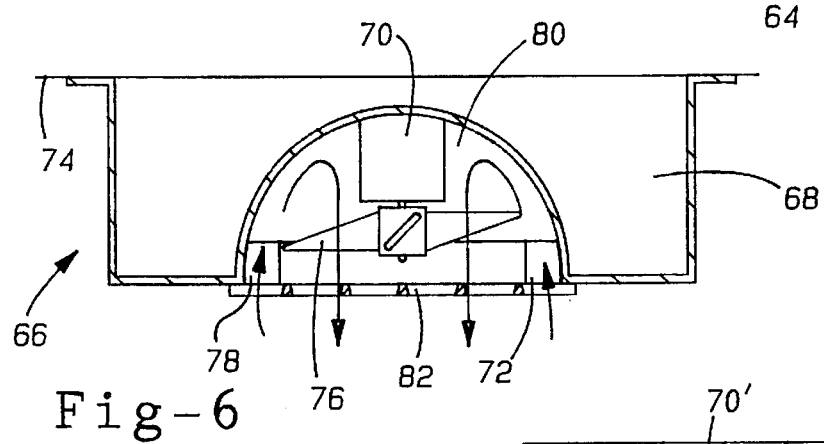
FIG. 6 is a sectional side view of yet another alternate embodiment of the present invention for use in conjunction with the ceiling of a room.
Figure 7:
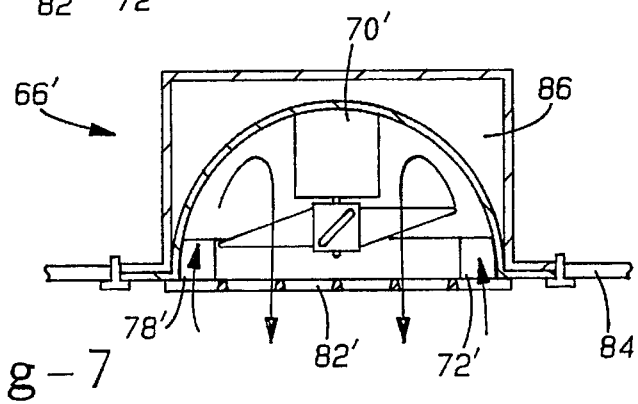
FIG. 7 is a sectional side view of a variation of the ceiling-mounted style of FIG. 8.

FIGS. 6 and 7 illustrate an additional embodiment of the present invention for integration with a ceiling of plaster-board or suspended construction.

With respect in particular to FIG. 6, a treater-circulator, generally illustrated as 66, is shown. The treater-circulator 66 includes a housing 68, a fan assembly 70, and an air treating component 72. The housing 68 is attached to a ceiling 74. The fan assembly 70 includes a blade 76. The air treating component 72 is like those discussed above, but is provided in a ring construction so as to more or less encircle the blade 76.

An air inlet 78 is defined in association with the component 72 so that the ring-shaped component 72 roughly fits in the inlet 78. The air is drawn into a plenum 80 by the rotating movement of the blade 76 and is forced out through an air outlet 82.

FIG. 7 illustrates an alternate version of the ceiling-mounted unit of the present invention. According to this construction, a treater-circulator 66' is integrally mounted within a suspended ceiling 84. A housing 86, a compacted version of the housing 68 of FIG. 6, is substantially disposed within the space above the ceiling 84. This embodiment also includes a fan assembly 70', an air-treating component 72', an inlet 78', and an outlet 82'.

Of course, more than one treater-circulator may be used in a room at a given time, or the various embodiments discussed above may be used in a single room in any combination to maximize air treatment and air circulation.

Figure 8:
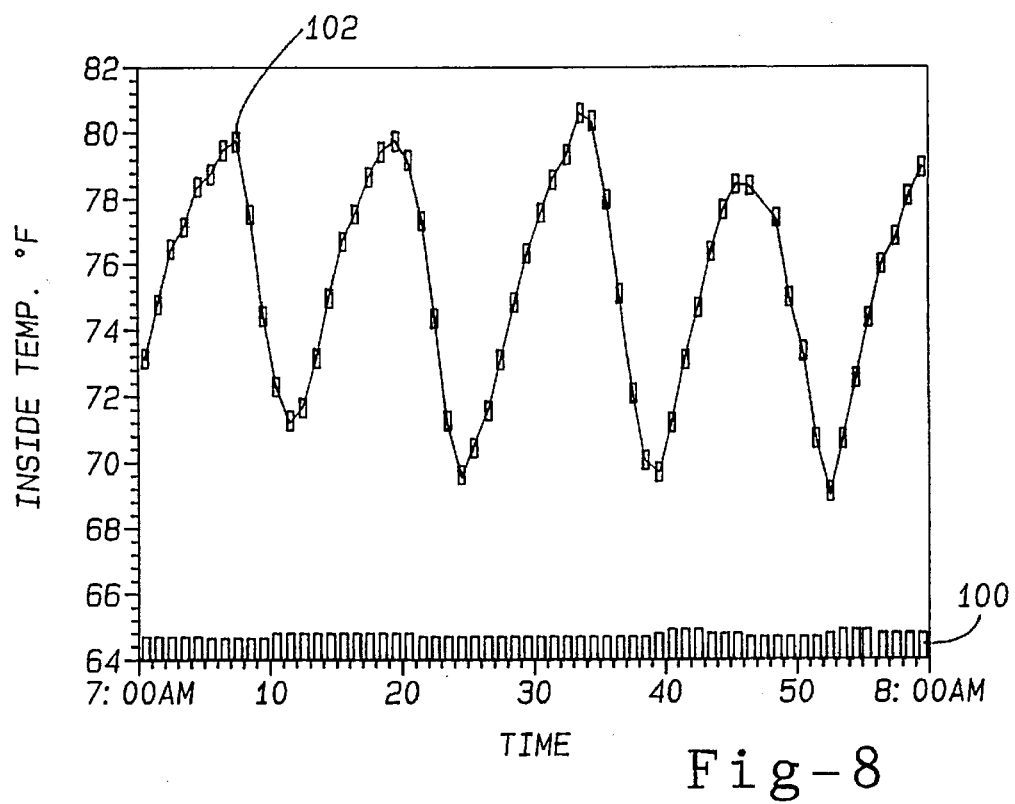
FIG. 8 is a chart showing ceiling and floor temperature variations in a typical room without the benefit of the air-temperature equalizing apparatus of the present invention.

FIG. 8 is a chart showing ceiling and floor temperature variations in a typical room without the benefit of air temperature equalizing of the present invention. The presented graph is based on temperature readings in a room measuring 50' by 50', the room having a 9' ceiling, two doors, and a glass wall. The readings were taken over the span of one hour during the winter in a northern state.

A lower bar graph 100 represents the temperature of the untreated room at a level just above the floor. The area above the bars 100 represents ambient air temperature. A series of 60 boxes 102 are provided on the line of the graph. These are increments of time of one minute each. Each of the lowest points of the valley of the line of the graph illustrates a "furnace on" point, while each of the highest points of the peak of the line represents a "furnace off" point. As illustrated, the space between the "furnace on" and "furnace off" points is, on the average, about 4 minutes, while the average floor temperature is about 64.8 degrees F.

Figure 9:
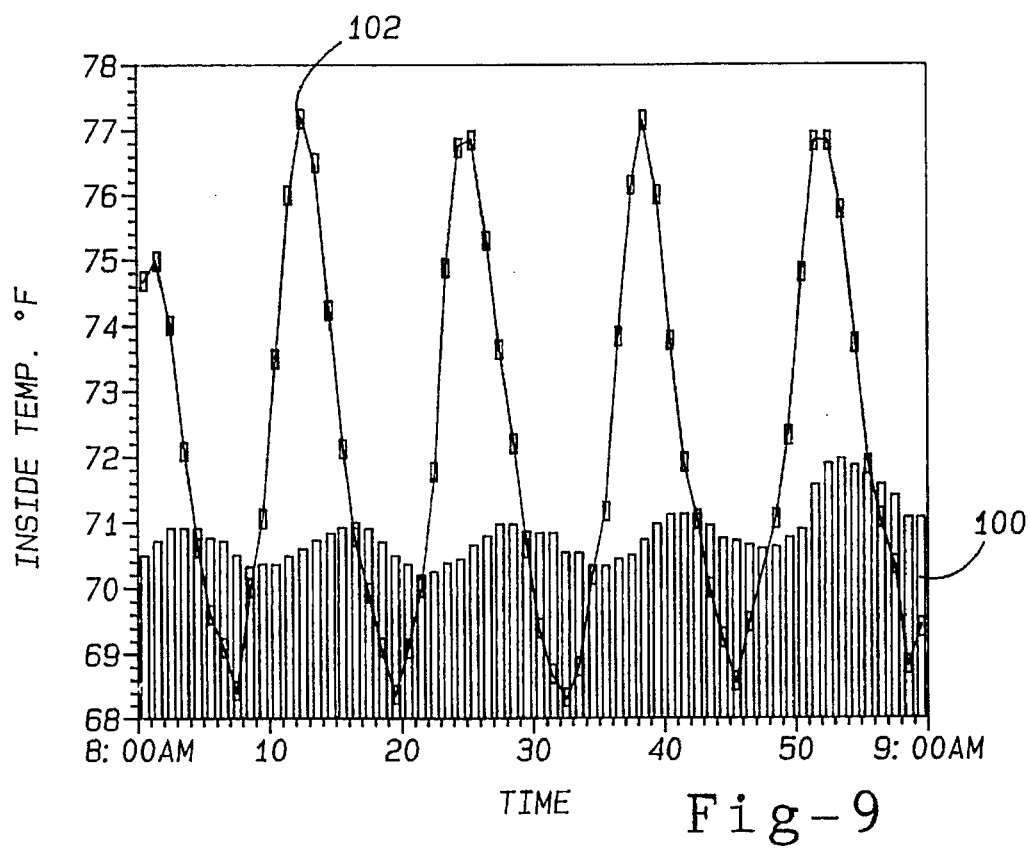
FIG. 9 is a chart similar to that of FIG. 4, but showing the differences brought about because of the use of the air-temperature equalizing unit of the present invention.

FIG. 9 represents a graph of readings taken from the same room as used in FIG. 8, but now an air treater-circulator of the present invention is operational in the room. As may be seen, the "furnace on" and "furnace off" points are spread from 4 minute intervals to 6 minute intervals, thus requiring less energy-consuming "furnace on" time. In addition, the average floor temperature is increased from 64.8 degrees F to about 70.6 degrees F, thus increasing the comfort zone of the subject room.

Having described my invention, however, many modifications thereto will become apparent to those skilled in the art to which it pertains without deviation from the spirit of the invention and as defined by the scope of the appended claims.

I claim:

1. A portable air treatment and circulation apparatus for use in a room for substantially balancing the ceiling-to-floor air temperature of the air distributed in the room and for improving the quality of the air in the room, said apparatus being positionable upon a ground surface and comprising:

a polygonal-shaped housing having a top, a bottom and an inner space established between said top and said bottom;

an air inlet formed across said bottom and an air outlet formed across said top, a cross-sectional area of said air inlet being equivalent to a cross-sectional area of said air outlet;

a plurality of set-offs elevating said air inlet a predetermined distance above the ground surface;

a fan assembly mounted within said inner space and power means for operating said fan assembly, said fan assembly including a plurality of fan blade portions which define, upon rotation, a blade path having a cross sectional area approximate to an area of both said inlet and outlet; and a planar shaped air treatment compound positioned substantially horizontally within said inner space in proximity to said fan assembly and extending across said cross-sectional area between said air inlet and said air outlet;

said fan assembly drawing untreated air upwardly into said housing through said air inlet, across said air treatment compound and exhausting treated air upwardly through said outlet.

2. The portable air treatment and circulation apparatus of claim 1, said air treatment compound further comprising a front wall, a back wall and a plurality of air passage holes formed between said front wall and said back wall for passage of air through said air treatment compound.

3. The portable air treatment and circulation apparatus of claim 2, further comprising a series of spaced apart passages between said front wall and said back wall of said air treatment compound.

4. The portable air treatment and circulation apparatus of claim 3, further comprising a granular air treatment media loosely disposed within said air treatment compound.

\* \* \* \* \*